US006669928B1

(12) United States Patent
Gurol

(10) Patent No.: US 6,669,928 B1
(45) Date of Patent: Dec. 30, 2003

(54) PERIODONTAL COMPOSITION

(75) Inventor: Ismail Macit Gurol, Seattle, WA (US)

(73) Assignee: TAMER International, Ltd., Seattle, WA (US)

( * ) Notice: Subject to any disclaimer, the term of this patent is extended or adjusted under 35 U.S.C. 154(b) by 0 days.

(21) Appl. No.: 10/287,577

(22) Filed: Oct. 31, 2002

Related U.S. Application Data

(63) Continuation of application No. 09/707,817, filed on May 4, 2000, now abandoned.
(60) Provisional application No. 60/134,248, filed on May 13, 1999.

(51) Int. Cl.[7] ................................................. A61K 7/16
(52) U.S. Cl. .......................... 424/49; 424/687; 424/688; 424/689; 424/692
(58) Field of Search ....................... 424/49, 687, 688, 424/689, 692

(56) References Cited

U.S. PATENT DOCUMENTS

| | | | | |
|---|---|---|---|---|
| 4,191,750 A | * | 3/1980 | Hodosh | 424/127 |
| 4,301,143 A | | 11/1981 | Barberio | 424/57 |
| 4,303,648 A | | 12/1981 | Witzel et al. | 424/158 |
| 4,358,437 A | | 11/1982 | Duke | 424/52 |
| 4,367,218 A | | 1/1983 | Jacobson | 424/49 |
| 4,438,102 A | * | 3/1984 | Ganci | 424/130 |
| 4,603,045 A | | 7/1986 | Smigel | 424/52 |
| 4,678,662 A | | 7/1987 | Chan | 424/57 |
| 4,708,965 A | * | 11/1987 | Morgan | 514/563 |
| 4,826,676 A | | 5/1989 | Gioffre et al. | 424/52 |
| 4,847,086 A | | 7/1989 | Knappwost | 424/687 |
| 4,871,396 A | | 10/1989 | Tsujita et al. | 424/49 |
| 5,000,942 A | | 3/1991 | Libin | 424/53 |
| 5,166,132 A | * | 11/1992 | Gordon | 514/2 |
| 5,427,768 A | | 6/1995 | Tung | 424/52 |
| 5,466,680 A | * | 11/1995 | Rudy | 514/57 |
| 5,585,391 A | * | 12/1996 | Carrell et al. | 514/357 |
| 5,645,821 A | | 7/1997 | Libin | 424/49 |
| 6,066,342 A | | 5/2000 | Gurol et al. | 424/687 |
| 6,099,868 A | * | 8/2000 | Hodosh | 424/600 |

OTHER PUBLICATIONS

Baker, K.A., "Oral Health Products," *Oral Health*, pp. 653–687, prior to May 13, 1999.
Baker, Karen A., *Oral Health Products*, Oral Health, pp. 653–687, prior to May 13, 1999.

* cited by examiner

*Primary Examiner*—Shep K. Rose
(74) *Attorney, Agent, or Firm*—Christensen O'Connor Johnson Kindness PLLC

(57) ABSTRACT

The present invention provides a periodontal composition compounded to include at least one alkaline agent to render a gel or paste having a pH of at least 9.0 to 11.0, and preferably 9.5 to 10.0. The preferred alkaline agent included in the composition is potassium hydroxide, and the composition preferably also includes aluminum hydroxide, calcium carbonate and magnesium carbonate. Of these agents, potassium hydroxide is the most basic compound utilized. Also suitably included in the composition (which can have the consistency of a liquid or suspension, but is preferably compounded as a stable gel or paste) are other excipients including: thickeners that are capable of withstanding the high pH environment without degradation (such as xanthane gum and microcrystalline cellulose); organoleptic agents such as gum arabic and polyethylene glycol; flavorings such as sodium chloride, acesulfame potassium, sodium saccharine, and mint flavorings; stabilizers such as colloidal silica; mild abrasive agents such as microcrystalline formed silica; a foaming agent such as sodium lauryl sulfate or sodium lauryl phosphate; and a fluoride compound such as sodium fluoride or sodium monofluorophosphate for anti-cavity effect.

20 Claims, No Drawings

PERIODONTAL COMPOSITION

CROSS-REFERENCES TO RELATED APPLICATIONS

The present application is a continuation of U.S. patent application Ser. No. 09/707,817, filed May 4, 2000, now abandoned, which claims the benefit of U.S. Provisional Application No. 60/134,248, filed May 13, 1999. Each of the above-identified applications is hereby incorporated herein by reference in its entirety.

FIELD OF THE INVENTION

The present invention relates to oral compositions for preventing and ameliorating periodontal disease, and particularly to toothpaste compositions.

BACKGROUND OF THE INVENTION

Many individuals suffer from gum disease, which can cause discomfort and, if left untreated, the loss of teeth. Gum, or periodontal, disease starts when bacteria normally present in the oral environment are allowed to multiply excessively, producing a sticky film referred to as plaque that coats the teeth. Plague that builds up along the gumline can cause gingivitis, or gum inflammation, particularly if the plaque remains and hardens into tartar. The failure to conscientiously remove the plaque through brushing and flossing and regular cleaning by dental professionals can lead to periodontitis. Normal methods of treatment of periodontitis include planing and scaling of pockets to remove deep plaque and tartar, and/or the local application of local antibiotics. Among the bacteria found normally in the mouth, predominantly six types live at the interface of the gum tissue and the teeth. Five of these bacteria consume sugars and lactose normally found in the mouth, and release lactic acid. The sixth bacteria, Veillonella, consumes lactic acid. Lactic acid generated by the bacteria slowly etches out the tooth enamel and tooth mass, thus creating pockets. More bacteria propagates into a larger space, eventually creating larger pockets. These bacterial pockets irritate the gum tissue, eventually causing bleeding and discomfort, leading the way for other types of bacteria to attack the bleeding gum tissue. This is believed to be the mechanism that starts periodontal disease.

In order to avoid the discomfort and potential loss of teeth caused by periodontitis, it is thus important to undertake daily dental cleaning. Most individuals utilize a tooth paste that includes a mild abrasive for daily brushing of their teeth. Commercially available toothpastes are compounded to include a mild abrasive, and are typically formulated with a pH that is slightly acidic or near neutral. Highly basic, i.e., high pH, tooth pastes are not commercially available.

An alkaline powder oral hygiene composition having a pH in excess of 9.0 has been disclosed by U.S. Pat. No. 5,645,821 to Libin. This reference further discloses formulating a paste or cream utilizing this composition. The composition includes magnesium hydroxide, calcium carbonate and magnesium carbonate in water with a gelling agent, such as glycerin, and an anionic surfactant. However, glycerin has been found by the present inventors to be unable to withstand the highly alkaline environment of such a composition for an extended period of time.

SUMMARY OF THE INVENTION

The present invention provides a periodontal composition compounded to include at least one alkaline agent to render a gel or paste having a pH of at least 9.0 to 11.0, and preferably 9.5 to 10.0. The preferred alkaline agent included in the composition is potassium hydroxide, and the composition preferably also includes calcium carbonate, magnesium carbonate and aluminum hydroxide. Of these agents, potassium hydroxide is the most basic compound utilized. Also suitably included in the composition (which can have the consistency of a liquid or suspension, but is preferably compounded as a stable gel or paste) are other excipients including: thickeners that are capable of withstanding the high pH environment without degradation (such as xanthane gum and microcrystalline cellulose); organoleptic agents such as gum arabic and polyethylene glycol; flavorings such as sodium or potassium chloride, acesulfame potassium, sodium saccharine, and mint flavorings; stabilizers such as colloidal silica; mild abrasive agents such as microcrystalline (not fumed) silica; a foaming agent such as sodium lauryl sulfate or sodium lauryl phosphate; and a fluoride compound such as stannous fluoride or sodium monofluorophosphate for anti-cavity effect.

The composition is believed to be effective at inhibiting periodontal disease caused by lactic acid-forming bacteria that thrive along the gumline and in gum pockets. The composition is also believed to be effective at reversing mild periodontal disease of this nature. The pH adjustment provided by the composition is believed to not only neutralize the acids formed by the bacteria, but also to inhibit the growth of the bacteria itself because periodontal bacteria thrives in an acidic environment, but not in the alkaline environment provided in accordance with the present invention. The composition has also been found effective at inhibiting and speeding the healing of canker sores.

DETAILED DESCRIPTION OF THE PREFERRED EMBODIMENT

The present invention provides an oral composition suitable for use in the maintenance of oral hygiene and the prevention and amelioration of periodontal disease. The invention is compounded to include at least one and preferably a plurality of alkaline agents, so as to have a pH prior to introduction into the oral environment of at least 9.0–11.0, and preferably 9.5–10.0. A pH of less than 10.5 is preferred to avoid irritation of gum tissues The composition is compounded as a liquid solution, suspension, gel or paste, and preferably as a gel or paste that is stable, for a period in excess of three months when stored at ambient conditions, without significant degradation of the gel or paste viscosity, despite the highly alkaline environment. The composition preferably includes potassium hydroxide, a strongly basic agent, that is capable of achieving the desired pH for the composition and retaining a high pH upon introduction into the oral environment. Specifically, the composition of the present preferred embodiment and having a pH of 9.5–10.0 will, after dilution in the oral environment, provide a resulting pH of at least 9.0 in the oral environment. In an aqueous composition, potassium hydroxide is included at 0.5 to 6% by weight, and preferably 1 to 6% by weight. In addition to potassium hydroxide, the composition preferably includes additional alkaline agents, preferably aluminum hydroxide, calcium carbonate and magnesium carbonate.

The acid-neutralizing oral composition of the present invention comprises alkaline (i.e., basic) substances and affords both rapid and long-lasting antacid activity in the mouth. As used herein, the term "antacid activity" refers to the ability of a substance to neutralize and/or to buffer an acid. Neutralization refers to a acid-base reaction by which an acid is made neutral. Neutralization does not necessarily mean attaining neutral pH (i.e., pH 7), rather, neutralization refers to the equivalence point for a particular acid-base reaction and will depend upon the respective strengths of the particular acid and base, their relative concentrations, and the buffering properties of the solution containing the acid and base. A buffer is a solution containing salts of weak acids that are capable of neutralizing both acids and bases and that act to maintain the pH of a solution. In other words, a buffered solution contains both a weak acid (e.g., acetic acid) and its conjugate weak base (e.g., sodium acetate) and its pH changes only slightly upon the addition of acid or base. The weak acid acts as a buffer when base is added to the solution, and the weak base acts as a buffer when acid is added to the solution. In the context of the present invention, the addition of an acid-neutralizing composition to an acidic oral environment particularly locally as the result of bacterial action, results in the neutralization of acids, thereby reducing the acidity of the oral environment along the gum line. At the same time, the oral environment becomes buffered, that is, the pH of the oral environment may be maintained, within limits, upon the subsequent addition of more acid from surviving bacteria.

Alkaline substances having long-lasting antacid activity include alkali and alkaline earth metal carbonates, such as calcium carbonate and magnesium carbonate, are suitable for use in the present invention. The rapid antacid effect of stronger alkaline substances such as alkali and alkaline earth metal hydroxides is also utilized in the present invention. Alkali and alkaline earth metal hydroxides suitable for use in the present invention include sodium, potassium and aluminum hydroxides, with potassium hydroxide being preferred for the present invention. The preferred embodiment of the present invention includes potassium hydroxide for rapid acid neutralization and one or more, and preferably all, of aluminum hydroxide, calcium carbonate and magnesium carbonate for residual acid reduction.

This composition is dissolved in water, and is then thickened with a thickener that is capable of withstanding the high pH environment without degradation during storage. Suitable thickeners include xanthane gum and microcrystalline cellulose (i.e., cellulose gum), which will withstand pH environments of up to 12.0 without substantial degradation. The composition of the present invention may alternately be compounded as a liquid suspension, however a more viscous gel or paste is preferred for application with a toothbrush. A stabilizer (suspension) agent such as colloidal silica may also be utilized.

In addition to alkaline agents and thickeners, the present invention may also include additional excipients. These include organoleptic agents, such as gum arabic and polyethylene glycol for mouthfeel, and flavorings such as sodium chloride, acesulfame, potassium, sodium, saccharine and mint flavorings. A foaming agent may optionally be included to create a foam in the oral cavity for better dispersion. Suitable foaming agents are sodium lauryl sulfate or sodium lauryl phosphate. Finally, it is recommended that the composition of the present invention either be compounded to include a fluoride compound, or be used in conjunction with a conventional fluoride containing toothpaste, so as to provide the anti-carey protection of fluoride. Suitable fluoride compounds for inclusion in the present invention are sodium fluoride or sodium monofluorophosphate. Other well known fluoride agents may be utilized. The composition of the present invention may be compounded to include any or all of these excipients, as desired.

A presently preferred composition, compounded in accordance with the present invention as an aqueous gel as set forth in Table I herein below. Suitable weight percent ranges for each of the elements included are also set forth in Table I.

TABLE I

Periodontal Gel Composition (Aqueous)

| Ingredient | Weight % Range | Preferred Weight % |
|---|---|---|
| Calcium Carbonate | 8–22 | 13.2 |
| Potassium Hydroxide | 0.5–6 | 1.03 |
| Magnesium Carbonate | 0.1–3 | 1.2 |
| Aluminum Hydroxide | 0.0–15.0 | 5.0 |
| Sodium Chloride | 0.5–1.5 | 0.13 |
| Potassium Chloride | 0–2 | 0.44 |
| Microcrystalline Fumed Silica | 0–2 | 0.1 |
| Xanthane Gum | 0.1–1 | 0.6 |
| Gum Arabic | 0–10 | — |
| Polyethylene Glycol | 0–3 | 0.3 |
| Colloidal Silica (SiO$_2$) | 0–2 | 0.4 |
| Carboxymethyl Cellulose Sodium (Solutab ™) | 1–15 | 2.2 |
| Microcrystalline Cellulose (Tabulose ™) | 1–15 | 3.5 |
| Sodium Saccharine | 0–5 | — |
| Acesulfame Potassium | 0–5 | 0.027 |
| Sodium Lauryl Phosphate | 0–5 | 0.2 |
| Spearmint Flavoring | 0–5 | 0.05 |
| Sodium Monofluorophosphate | 0–1 | 0.03 |
| Sodium Fluoride | 0–1 | — |
| Wintergreen Flavoring | 0–5 | 0.01 |

In addition to preventing periodontal disease and ameliorating mild periodontal disease, i.e., periodontal disease in which pockets have not yet formed that are so deep that the oral composition of the present invention cannot be introduced during normal brushing, the oral composition of the present invention is also suitable for use in prevention and amelioration of canker sores. Further, the oral composition of the present invention is believed to be potentially useful in the treatment of more serious periodontal disease, i.e., periodontal disease with deep pockets, if the composition is introduced into such deep pockets, such as by introduction under a fluid pressure through an irrigating device.

The oral composition of the present invention may be utilized in combination with a secondary antibacterial composition, specifically a liquid in which a user's toothbrush is stored in between brushing. This liquid can suitably be a saline solution consisting of sodium chloride dissolved in hydrogen peroxide. Both of these agents have antimicrobial activity. Inserting a toothbrush into such a solution in between use, and then applying the gel composition of the present invention to a toothbrush that is wetted with the solution prior to application into the oral cavity is believed to be desirable in inhibiting periodontal disease.

The oral composition of the present invention is suitably used at least two times a day, as a brushing compound such as after breakfast and before bedtime. Preferably a user of the oral composition of the present invention does not rinse out the composition from his or her mouth after application, for better residual acid reduction.

The composition of the present invention is thus useful at reducing the lactic acid and similar organic acids produced by periodontal bacteria, e.g., mouth flora. The composition of the present invention neutralizes the acids produced by these bacteria, and in addition, most bacteria are unable to survive the high pH environment created upon application of the present composition. Thus, in addition to neutralizing acids produced by bacteria, proliferation of the bacteria itself is reduced or inhibited due to the inability of the bacteria to thrive. Other bacteria present in the oral cavity, such as Veillonella bacteria, consume lactic acid produced by other bacteria. These bacteria are also controlled by the application of the composition of the present invention because the elimination of lactic acid causes these bacteria to be unable to thrive. Unlike conventional antibiotic treatment, it is not expected that periodontal bacteria will develop resistance to the composition of the present invention.

While the preferred embodiment of the invention has been illustrated and described, it will be apparent that various changes can be made therein without departing from the spirit and scope of the invention.

The embodiments of the invention in which an exclusive property or privilege is claimed are defined as follows:

1. A method of treating an individual's periodontal disease, comprising applying to the individual's oral cavity a composition comprising potassium hydroxide in a liquid carrier, the composition having a pH of about 9.0 to about 11.0, wherein the composition is free of glycerin.

2. The method of claim 1, comprising periodically applying the composition.

3. The method of claim 2, comprising applying the composition daily for a predetermined time period.

4. The method of claim 1, wherein the composition is applied in a pressurized irrigation stream to a pocket between the individual's teeth and gum.

5. The method of claim 1, wherein the composition is applied with a tooth brush, further comprising storing the toothbrush in an antimicrobial medium between multiple applications.

6. The method of claim 1, wherein the composition that is applied has a pH of about 9.5 to about 10.0.

7. The method of claim 1, wherein immediately after application of the composition to the oral cavity, the pH of the oral cavity is at least about 9.0.

8. The method of claim 1, wherein the composition that is applied comprises potassium hydroxide at a level of about 0.5 to about 6.0% by weight.

9. The method of claim 8, wherein the composition that is applied comprises potassium hydroxide at a level of about 1.0 to about 6.0% by weight.

10. The method of claim 1, wherein the composition that is applied further comprises at least one additional alkaline agent selected from the group consisting of aluminum hydroxide, calcium carbonate, magnesium carbonate and mixtures thereof.

11. The method of claim 10, wherein the composition that is applied comprises calcium carbonate at a level of about 8 to about 22% by weight and magnesium carbonate at a level of about 0.1 to about 3.0% by weight.

12. The method of claim 1, wherein the liquid carrier comprises water.

13. The method of claim 1, wherein the composition applied is compounded as a gel, paste, liquid or suspension.

14. The method of claim 1, wherein the composition that is applied further comprises a thickening agent that is stable at the pH of the composition of at least about 9.0.

15. The method of claim 14, wherein the thickening agent is at least one of xanthane gum or microcrystalline cellulose.

16. The method of claim 1, wherein the composition that is applied further comprises at least one excipient selected from the group consisting of organoleptic agents, stabilizers, thickening agents, abrasives, foaming agents, fluoride compounds and flavoring agents, the at least one excipient being stable at the pH of the composition of at least about 9.0.

17. A method of treating an individual's periodontal disease, comprising periodically applying to the individual's oral cavity a composition comprising potassium hydroxide in an amount sufficient to ameliorate the periodontal disease, wherein the composition is free of glycerin.

18. A method of treating an individual's periodontal disease, comprising applying to the individual's oral cavity a composition comprising an alkali metal hydroxide in a liquid carrier in an amount sufficient to yield a composition pH of about 9.0 to about 11.0, wherein the composition is free of glycerin.

19. The method of claim 18, wherein the alkali metal hydroxide in the composition is at least one of potassium hydroxide or sodium hydroxide.

20. A method of treating an individual's periodontal disease, comprising applying to the individual's oral cavity a composition comprising potassium hydroxide in a liquid carrier in an amount sufficient to ameliorate the periodontal disease, wherein the composition is free of glycerin.

* * * * *

UNITED STATES PATENT AND TRADEMARK OFFICE
CERTIFICATE OF CORRECTION

PATENT NO.    : 6,669,928 B1
DATED         : December 30, 2003
INVENTOR(S)   : I.M. Gurol It is certified that error appears in the above-identified patent and that said Letters Patent is hereby corrected as shown below:

<u>Title page,</u>
Item [56], References Cited, OTHER PUBLICATIONS, delete as duplicative "Baker, Karen A., *Oral Health Products*, Oral Health, pp. 653-687, prior to May 13, 1999."

Signed and Sealed this

Eleventh Day of May, 2004

JON W. DUDAS
*Acting Director of the United States Patent and Trademark Office*